United States Patent
Parker et al.

(10) Patent No.: US 10,473,595 B2
(45) Date of Patent: Nov. 12, 2019

(54) APPARATUS AND METHOD FOR MEASURING A COMPOSITION OF A FLUID

(71) Applicant: M-Flow Technologies Ltd, Abingdon (GB)

(72) Inventors: Alan Parker, Abingdon (GB); Giles Edward, Abingdon (GB); Alex Wall-Clarke, Abingdon (GB); Arnault Tremolet, Abingdon (GB)

(73) Assignee: M-Flow Technologies Ltd, Abingdon (GB)

(*) Notice: Subject to any disclaimer, the term of this patent is extended or adjusted under 35 U.S.C. 154(b) by 330 days.

(21) Appl. No.: 15/429,785

(22) Filed: Feb. 10, 2017

(65) Prior Publication Data

US 2017/0248530 A1 Aug. 31, 2017

(30) Foreign Application Priority Data

Feb. 11, 2016 (GB) .................... 1602443.2

(51) Int. Cl.
*G01N 22/00* (2006.01)
*G01N 33/28* (2006.01)
*G01N 22/04* (2006.01)

(52) U.S. Cl.
CPC .......... *G01N 22/00* (2013.01); *G01N 22/04* (2013.01); *G01N 33/2823* (2013.01)

(58) Field of Classification Search
CPC ........ G01N 22/00; G01N 22/04; G01N 33/18; G01N 33/1833; G01N 33/28; G01N 33/2823; G01N 21/3581; G01R 31/2822
See application file for complete search history.

(56) References Cited

U.S. PATENT DOCUMENTS

| 4,651,085 A | 3/1987 | Sakurai et al. | |
|---|---|---|---|
| 2013/0033272 A1* | 2/2013 | Folgeroe | G01N 22/00 324/637 |
| 2013/0270431 A1* | 10/2013 | Minette | G01V 5/12 250/269.3 |
| 2014/0182737 A1* | 7/2014 | Jones | G01N 22/00 138/177 |
| 2016/0146743 A1* | 5/2016 | Edward | G01N 22/00 73/61.45 |

FOREIGN PATENT DOCUMENTS

| SU | 1719973 | 3/1992 |
|---|---|---|
| WO | WO 90/04167 | 4/1990 |
| WO | WO 02/16931 | 2/2002 |

* cited by examiner

*Primary Examiner* — Son T Le
(74) *Attorney, Agent, or Firm* — Levy & Grandinetti

(57) ABSTRACT

An apparatus for measuring a composition of a fluid has a fluid conduit with a wall defining a fluid flow path, a transmitting antenna, a receiving antenna, and an electrically conductive waveguide member for electromagnetic coupling with the transmitting antenna and the receiving antenna and for guiding an electromagnetic field from the transmitting antenna to the receiving antenna along a waveguide path. The waveguide member is separated from the fluid flow path by an electrically insulating inner region of the wall. The waveguide member defines an opening disposed towards the fluid flow path to permit a portion of the electromagnetic field to extend through the opening and the inner region of the wall into the fluid flow path.

73 Claims, 11 Drawing Sheets

APPARATUS AND METHOD FOR MEASURING A COMPOSITION OF A FLUID

FIELD

The present invention relates to an apparatus and method for measuring a composition of a fluid and, in particular though not exclusively, for measuring the proportion of water in the liquid content of a two- or three-phase fluid produced from an oil or gas well.

BACKGROUND

It may be desirable in some technical fields to measure the composition of a fluid flowing through a fluid conduit. For example, in the oil and gas industry, it may be desirable to measure the composition of a two- or three-phase fluid produced from an oil or gas well. In particular, it may be desirable to accurately measure the proportion of water by volume in the liquid phase, also known as the water-cut, of a two- or three-phase fluid produced from an oil or gas well.

It is known to use a meter which comprises a cavity resonant at radio frequencies to determine a composition of a fluid and, in particular, to determine the water-cut of a two- or three-phase fluid from measurements of one or more properties of one or more resonant electromagnetic modes of the cavity. However, such resonant electromagnetic measurements can become more difficult or less accurate at higher water-cut values in the range of 50%-100% due to the absorption of electromagnetic energy at radio frequencies in water and, in particular, in saline water. This is particularly the case for water-continuous fluid flows where the water cut is sufficiently high that the liquid part of the fluid flow can be regarded as water containing enclosed areas of a liquid other than water such as enclosed areas of oil.

SUMMARY

It should be understood that one or more of the features of any one or more of the following aspects or embodiments may apply alone or in any combination in relation to any of the other aspects or embodiments.

According to a first aspect or a first embodiment of the present invention there is provided an apparatus for measuring a composition of a fluid, comprising:

a fluid conduit having a wall which defines a fluid flow path;
a transmitting antenna;
a receiving antenna; and
an electrically conductive waveguide member configured for electromagnetic coupling with the transmitting antenna and the receiving antenna and for guiding an electromagnetic field from the transmitting antenna to the receiving antenna along a waveguide path, wherein the waveguide member is separated from the fluid flow path by an electrically insulating inner region of the wall and the waveguide member defines an opening which is disposed towards the fluid flow path to permit a portion of the electromagnetic field to extend through the opening and the inner region of the wall into the fluid flow path.

In use, an input electrical signal may be provided to the transmitting antenna and an output electrical signal measured at the receiving antenna. An electromagnetic loss may be determined from the input electrical signal and the output electrical signal. A composition of the fluid present in and/or flowing through the flow path may be determined from the electromagnetic loss and a known relationship between the composition of the fluid and the electromagnetic loss. Such an apparatus may provide protection for the waveguide member from any fluids present in and/or flowing through the fluid flow path whilst still permitting the guided electromagnetic field to interact with any fluids present in and/or flowing through the fluid flow path.

The waveguide member may be electrically insulated from the transmitting antenna and the receiving antenna.

The waveguide member may define a channel or a groove dispelled towards the fluid flow path and the channel or the groove defines the opening.

The opening may extend along the whole of the waveguide path.

The opening may extend along part of the waveguide path.

The waveguide member may have a generally uniform cross-section.

The waveguide member may have a generally U-shaped cross-section.

The waveguide member may have a generally rectangular or a generally square cross-section.

The waveguide member may have a generally circular cross section.

The channel or groove may have a generally rectangular or a generally square cross-section.

The channel or groove may have a generally circular cross-section.

At least one of the configuration of the waveguide member, a thickness of the inner region of the wall, a material of the inner region of the wall and a frequency of the electromagnetic field may be selected so as to permit the electromagnetic field to extend through the opening and the inner region of the wall into the fluid flow path.

The waveguide path may extend along and/or around the fluid flow path.

The waveguide path may extend along a straight line or may comprise a section which extends along a straight line.

The waveguide path may extend along a circular arc or may comprise a section which extends along a circular arc.

The waveguide path may be circular or may comprise a section which is circular.

The waveguide path may encircle or circumscribe the fluid flow path one or more times or may comprise a section which encircles or circumscribes the fluid flow path one or more times. Such a waveguide path may increase the interaction between the guided electromagnetic field and any fluid present in and/or flowing through the fluid flow path leading to a more sensitive measurement of fluid composition.

The waveguide path may be helical or generally helical or may comprise a section which is helical or generally helical.

The waveguide path may extend parallel to a longitudinal axis of the fluid conduit or may comprise a section which extends parallel to the longitudinal axis of the fluid conduit.

The waveguide path may extend circumferentially relative to the longitudinal axis of the fluid conduit or may comprise a section which extends circumferentially relative to the longitudinal axis of the fluid conduit.

The waveguide path may encircle or circumscribe the longitudinal axis of the fluid conduit one or more times or may comprise a section which encircles or circumscribes the longitudinal axis of the fluid conduit one or more times. Such a waveguide path may increase the interaction between the guided electromagnetic field and any fluid present in and/or flowing through the fluid flow path leading to a more sensitive measurement of fluid composition.

The waveguide path may extend helically or generally helically relative to the longitudinal axis of the fluid conduit or may comprise a section which extends helically or generally helically relative to the longitudinal axis of the fluid conduit.

The inner region of the wall may seal the waveguide member from the fluid flow path.

The wall ray define a continuous inner which defines the fluid flow path.

The transmitting antenna may be at least partially located and/or embedded within the wall.

The receiving antenna may be at least partially located and/or embedded within the wall.

The waveguide member may be at least partially located and/or embedded within the wall.

The waveguide member may define part of the wall.

The waveguide member may comprise a metal.

The waveguide member may comprise at least one of copper, nickel, tin, aluminium, zinc, iron, silver and gold.

The waveguide member may comprise an electrically conductive layer or coating.

The waveguide member may comprise a layer of electrically conductive paint.

The waveguide member may comprise a layer of carbon graphite.

The waveguide member may comprise a layer of an electrically conductive spray-on material such as an electrically conductive spray-on polymer.

The waveguide member may comprise a layer of carbon spray-on polymer.

The inner region of the wall between the waveguide member and the fluid flow path may comprise a dielectric material.

The inner region of the wall between the waveguide member and the fluid flow path may comprise an electrically insulating material.

The inner region of the wall between the waveguide ember and the fluid flow path may comprise one or more electrically insulating reinforcing elements embedded the electrically insulating material.

The one or more electrically insulating reinforcing elements of the inner region of the wall may comprise one or more polymeric fibres, aramid fibres, non-polymeric fibres, basalt fibres, glass fibres and/or E-glass fibres.

The waveguide member may comprise an electrically conductive composite material comprising an electrically insulating material and one or more electrically conductive reinforcing elements embedded within the electrically insulating material.

The electrically insulating material of the waveguide member may comprise the same electrically insulating material as the inner region of the wall between the waveguide member and the fluid flow path.

The electrically insulating material of the waveguide member may be continuous with the electrically insulating material of the inner region of the wall between the waveguide member and the fluid flow path.

The one or more electrically conductive reinforcing elements of the waveguide member may comprise one or more carbon fibres.

The one or more electrically conductive reinforcing elements of the waveguide member may have a common orientation relative to the waveguide path. For example, the one or more electrically conductive reinforcing elements may be arranged generally parallel to the waveguide path.

The wall may comprise an outer region.

The outer region of the wall may be located externally of the waveguide member.

The outer region of the wall may be electrically conductive.

The outer region of the wall may define at least part of the waveguide member.

The outer region of the wall may be electrically insulating.

The outer region of the wall may comprise an electrically insulating material and one or more reinforcing elements embedded within the electrically insulating material.

The electrically insulating material of the outer region of the wall may comprise the same electrically insulating material as the waveguide member.

The electrically insulating material of the outer region of the wall may be continuous with the electrically insulating material of the waveguide member.

The one or more reinforcing elements of the outer region of the wall may be electrically insulating.

The one or more reinforcing elements outer region of the wall may comprise one or more polymeric fibres, aramid fibres, non-polymeric fibres, basalt fibres, glass fibres and/or E-glass fibres.

The one or more reinforcing element of the outer region of the wall may be electrically conductive.

The one or more reinforcing elements of the outer region of the wall may comprise one or more carbon fibres.

The fluid conduit may comprise a base member.

The base member may comprise the same electrically insulating material the electrically insulating inner region of the wall.

The base member may define the electrically insulating inner region of the wall.

The base member may be generally tubular.

The base member may comprise a sleeve.

The waveguide member may be located externally of the base member.

The transmitting antenna may be located externally of the base member.

The receiving antenna may be located externally of the base member.

The waveguide path may extend along and/or around the base member.

The waveguide path may encircle or circumscribes the base member one or more times.

The waveguide path may extend helically or generally helically around the base member.

The waveguide member may define a channel or a groove having an opening is disposed towards the base member.

The fluid conduit may comprise an electrically insulating waveguide filler member.

The waveguide filler member may extend from an outer surface of the base member into the channel or the groove defined by the waveguide member.

The waveguide filler member may extend from the outer surface of the base member to an inner surface of the channel or the groove defined by the waveguide member.

The waveguide filler member may fill the channel or the groove defined by the waveguide member.

The waveguide filler member may be formed in situ on, over and/or around the base member.

The waveguide filler member may be formed separately from the base member and is then fitted on, over and/or around the base member.

The waveguide filler member may be bonded, adhered, fused, welded and/or joined to the base member.

The waveguide filler member may comprise the same electrically insulating material as the base member.

The electrically insulating material of the waveguide filler member may be continuous with the electrically insulating material of the base member.

The waveguide filler member and the base member may be unitary.

The transmitting antenna may extend into and/or may be at least partially embedded within the waveguide filler member.

The receiving antenna may extend into and/or may be at least partially embedded within the waveguide filler member.

The fluid conduit may comprise a plurality electrically insulating waveguide filler members.

Each waveguide filler member may extend from an outer surface of the base member into the channel or the groove defined by the waveguide member.

The waveguide member may be formed in situ on, over and/or around the waveguide filler member.

The waveguide member may be formed separately from the waveguide filler member and may then be fitted on, over and/or around the waveguide filler member.

The waveguide member may be bonded, adhered, fused, welded and/or joined to the waveguide filler member.

The waveguide member and the waveguide filler member may be unitary.

The waveguide filler member may comprise the same electrically insulating material as the waveguide member.

The electrically insulating material of the waveguide filler member may be continuous with the electrically insulating material of the waveguide member.

The fluid conduit may comprise an outer member.

The outer member may comprise the same material as the outer region of the wall.

The outer member may define the outer region of the wall.

The outer member may be formed in situ on, over and/or around the waveguide member.

The outer member may be formed separately from the waveguide member and may then be fitted on, over and/or around the waveguide member.

The outer member may be bonded, adhered, fused, welded and/or joined to the waveguide member.

The outer member may comprise an electrically insulating material and one or more reinforcing elements embedded within the electrically insulating material.

The electrically insulating material of the outer member may comprise the same electrically insulating material as the waveguide member.

The electrically insulating material of the outer member may continuous with the electrically insulating material of the waveguide member.

The outer member and the waveguide member may be unitary.

The one or more reinforcing elements of the outer member may be electrically conductive.

The one or more reinforcing elements of the outer member may comprise one or more carbon fibres.

The fluid conduit may be configured to withstand one or more environmental conditions associated with a fluid in an oil or gas well.

The fluid conduit may be configured to withstand a pressure within the fluid flow path of up to 15,000 PSI, up to 10,000 PSI, or up to 5,000 PSI.

The fluid conduit may be configured to withstand a temperature within the fluid flow path of up to 200° C., of up to 150° C. or of up to 100° C.

The apparatus may comprise an electrical signal generator connected electrically to the transmitting antenna.

The apparatus may comprise an electrical signal detector connected electrically to the receiving antenna.

The apparatus may comprise a controller.

The controller may be configured to measure an input electrical signal provided by the electrical signal generator to the transmitting antenna.

The controller may be configured to measure an output electrical signal received by the electrical signal detector from the receiving antenna.

The controller may be configured to determine an electromagnetic loss from the measured input electrical signal and the measured output electrical signal.

The controller may be configured to determine the composition of the fluid from the determined electromagnetic loss and a known relationship between the composition of the fluid and the electromagnetic loss.

The apparatus may comprise a temperature sensor for measuring a temperature of the fluid. For example, the fluid conduit may comprise a temperature sensor for measuring a temperature of the fluid and/or a temperature of the wall adjacent to the fluid flow path. The temperature sensor may be at least partially located and/or embedded within the wall.

The controller may be configured to determine the composition of the fluid from the determined electromagnetic loss and the measured temperature, and a known relationship between the composition of the fluid, the electromagnetic loss and the temperature.

The apparatus may comprise a sensor measuring a salinity of the fluid. For example, the fluid conduit may comprise a sensor for measuring a salinity of the fluid. The sensor for measuring the salinity of the fluid may be at least partially located and/or embedded within the wall.

The controller may be configured to determine the composition of the fluid from the determined electromagnetic loss and the measured salinity, and a known relationship between the composition of the fluid, the electromagnetic loss and the salinity.

The controller may be configured to determine the composition of the fluid from the determined electromagnetic loss, the measured temperature and the measured salinity, and a known relationship between the composition of the fluid, the electromagnetic loss, the temperature and the salinity.

The apparatus may comprise:
a plurality of transmitting antennae;
a plurality of a receiving antennae; and
a plurality of electrically conductive waveguide members.

Each waveguide member may be configured for electromagnetically coupling with a corresponding one of the transmitting antennae and a corresponding one of the receiving antennae and for guiding a corresponding electromagnetic field from the corresponding transmitting antenna to the corresponding receiving antenna along a corresponding waveguide path.

Each waveguide member may be separated from the fluid flow path by the electrically insulating inner region of the wall.

Each waveguide member may define a corresponding opening which is disposed towards the fluid flow path to permit a portion of the corresponding electromagnetic field to extend through the corresponding opening and the inner region of the wall into the fluid flow path.

The use of a plurality of electrically conductive waveguide members, each electrically conductive waveguide member being configured to guide a corresponding electromagnetic field along a different waveguide path to each of the other electrically conductive waveguide members, may permit the determination of a plurality of electromagnetic loss values, each loss value corresponding to a different waveguide path. This may permit different fluid compositions to be determined for different regions of the flow path from the electromagnetic loss values, wherein each region of the flow path is adjacent to a corresponding one of the waveguide paths. This may also permit an average composition of the fluid to be determined from the determined fluid compositions.

At least one of the waveguide paths may extend along and; or around the fluid flow path.

At least one of the waveguide paths may extend along a straight line or may comprise a section which extends along a straight line.

At least one of the waveguide paths may extend along a circular arc or may comprise a section which extends along a circular arc.

At least one of the waveguide paths may be circular or may comprise a section which is circular.

At least one of the waveguide paths may encircle or circumscribe the fluid flow path one or more times or may comprise a section which encircles or circumscribes the fluid flow path one or more tunes. Such a waveguide path may increase the interaction between the guided electromagnetic field and any fluid present in and/or flowing through the fluid flow path leading to a more sensitive measurement of fluid composition.

At least n of the waveguide paths may be helical or generally helical or may comprise a section which is helical or generally helical.

At least one of the waveguide paths may extend parallel to a longitudinal axis of the fluid conduit or may comprise a section which extends parallel the longitudinal axis of the fluid conduit.

A first one of the waveguide paths may extend parallel to the longitudinal axis of the fluid conduit along a first side of the fluid conduit and a second one of the waveguide paths may extend parallel to the longitudinal axis of the fluid conduit along a second side of the fluid conduit which is opposite, for example diametrically opposite, to the first side of the fluid conduit. In use, such an apparatus may provide an indication of flow stratification in a fluid flowing through the fluid flow path.

At least one of the waveguide paths may extend circumferentially relative the longitudinal axis of the fluid conduit or may comprise a section which extends circumferentially relative to the longitudinal axis of the fluid conduit.

A first one of the waveguide paths may extend circumferentially relative to the longitudinal axis of the fluid conduit at a first axial position of the fluid conduit and a second one of the waveguide paths may extend circumferentially relative to the longitudinal axis of the fluid conduit at a second axial position of the fluid conduit, wherein the first and second axial positions are axially separated. In use, such an apparatus may provide an indication of axial changes in fluid composition and/or in a fluid flowing through the fluid flow path.

At least one of the waveguide paths may encircle or circumscribe the longitudinal axis of the fluid conduit one or more times or may comprise a section which encircles or circumscribes the longitudinal axis of the fluid conduit one or more times. Such a waveguide path may increase the interaction between the guided electromagnetic field and any fluid present in and/or flowing through the fluid flow path leading to a more sensitive measurement of fluid composition.

At least one of the waveguide paths may extend helically or generally helically relative to the longitudinal axis of the fluid conduit or may comprise a section which extends helically or generally helically relative to the longitudinal axis of the fluid conduit.

A first one of the waveguide paths may extend helically or generally helically relative to the longitudinal axis of the fluid conduit and a second one of the waveguide paths may extend helically or generally helically relative to the longitudinal axis of the fluid conduit, wherein the first and second waveguide paths are generally parallel to one another but axially spaced apart.

The electromagnetic field may have radio frequency (RF), for example the electromagnetic energy may have a frequency in the range 1 to 10 GHz, 2.5 to 7.5 GHz, 4 to 6 GHz or a frequency of approximately 5 GHz.

At least one of the inner region of the wall, the waveguide member, the waveguide filler member, the outer region of the wall and the outer member may comprise at least one of a polymer material, a thermoplastic material, a thermoset material, a polyaryl ether ketone, a polyaryl ketone, a polyether ketone (PEK), a polyether ether ketone (PEEK), a polycarbonate, polyvinyl chloride (PVC), a polyamide, polyamide 11 (PA11), polyvinylidene fluoride, polyvinylidene difluoride (PVDF), polyphenylene suphide (PPS), polyethylenimines (PEI), polyoxymnethylene (POM), acetal, a resin, a setting resin, a polymeric resin, and an epoxy resin.

According to a second aspect or a second embodiment of the present invention there is provided a method for measuring a composition of a fluid, the method comprising:

providing a fluid in a fluid flow path defined by a wall of a fluid conduit;

electromagnetically coupling a transmitting antenna and a receiving antenna with an electrically conductive waveguide member;

guiding an electromagnetic field from the transmitting antenna to the receiving antenna along a waveguide path defined by the waveguide member.

wherein the waveguide member is separated from the fluid flow path by an electrically insulating inner region of the wall and the waveguide merrier defines an opening which is disposed towards the fluid flow path to permit a portion of the electromagnetic field to extend through the opening and the inner region of the wall into the fluid flow path.

The method may comprise:

providing an input electrical signal to the transmitting antenna; and measuring an output electrical signal at the receiving antenna.

The method may comprise determining a composition of the fluid from the input and output electrical signals.

The method may comprise determining an electromagnetic loss from the input electrical signal and the measured output electrical signal.

The method may comprise determining the composition of the fluid from the determined electromagnetic loss and a known relationship between the composition of the fluid and the electromagnetic loss.

The method may comprise determining the relative proportions of different liquid components of the fluid from the determined electromagnetic loss and a known relationship between the relative proportions of the different liquid components and the electromagnetic loss.

The method may comprise determining the proportion of water by volume in the liquid phase of the fluid from the determined electromagnetic loss and a known relationship between the proportion of water by volume in the liquid phase of the fluid and the electromagnetic loss.

The method may comprise measuring a temperature of the fluid and/or a temperature of the wall adjacent to the fluid flow path.

The method may comprise determining the composition of the fluid from the determined electromagnetic loss and the measured temperature, and a known relationship between the composition of the fluid, the electromagnetic loss and the temperature.

The method may comprise measuring a salinity of the fluid.

The method may comprise determining the composition of the fluid from the determined electromagnetic loss and the measured salinity, and a known relationship between the composition of the fluid, the electromagnetic loss and the salinity.

The method may comprise measuring a salinity of the fluid, a temperature of the fluid and/or a temperature of the wall adjacent to the fluid flow path.

The method may comprise determining the composition of the fluid from the determined electromagnetic loss, the measured temperature and the measured salinity, and a known relationship between the composition of the fluid, the electromagnetic loss, the temperature and the salinity.

The input and output electrical signals may be radiofrequency (RF) electrical signals.

The input and output electrical signals may have a frequency in the range 1 to 10 GHz, 2.5 to 7.5 GHz, 4 to 6 GHz or a frequency of approximately 5 GHz.

The fluid may be a two-phase fluid or a three-phase fluid.

The fluid may comprise water.

The fluid may comprise oil and/or gas.

The fluid may comprise a mixture of liquids of which the proportion of water is in the range 50% to 100%.

The method may comprise orienting the fluid conduit vertically or near vertically. Orienting the fluid conduit vertically or near vertically may enhance the degree mixing of different fluids present in or flowing through the fluid flow path. Additionally or alternatively, orienting the fluid conduit vertically or near vertically may result in the liquid phases of a three phase fluid on or closer to the wall of the fluid conduit.

The method may comprise orienting the fluid conduit horizontally.

The method may comprise inclining the fluid conduit between a vertical and a horizontal orientation.

The method may comprise mixing the fluid present in and/or flowing through the fluid flow path.

According to a third aspect or a third embodiment of the present invention there is provided a method for manufacturing an apparatus for measuring a composition of a fluid, the method comprising:

providing a fluid conduit having a defines a fluid flow path:

providing a transmitting antenna;

providing a receiving antenna; and providing an electrically conductive waveguide member which is configured for electromagnetic coupling with the transmitting antenna and the receiving antenna and for guiding an electromagnetic field from the transmitting antenna to the receiving antenna along a waveguide path, and wherein the waveguide member is separated from the fluid flow path by an electrically insulating inner region of the wall and the waveguide member defines an opening which is disposed towards the fluid flow path to permit a portion of the electromagnetic field to extend through the opening and the inner region of the wall into the fluid flow path.

The method may comprise selecting at least one of the configuration of the waveguide member, a thickness of the inner region of the wall, a material of the inner region of the wall and a frequency of the electromagnetic field so as to permit the electromagnetic field to extend through the opening and the inner region of the wall into the fluid flow path.

The method may comprise at least partially locating and/or embedding the transmitting antenna within the wall.

The method may comprise at least partially locating and/or embedding the receiving antenna within the wall.

The electrically conductive waveguide member may define part of the wall.

The electrically conductive waveguide member may be at least partially located and/or embedded within the wall.

The method may comprise providing an electrically insulating base member which defines the fluid flow path.

The base member may comprise an electrically insulating material.

The base member may comprise an electrically insulating material and one or more reinforcing elements embedded within the electrically insulating material.

The one or more reinforcing elements may be electrically insulating.

The one or more reinforcing elements may comprise at least one of polymeric fibres, aramid fibres, non-polymeric fibres, basalt fibres, glass fibres and E-glass fibres.

The method may comprise forming n electrically conductive intermediate layer in situ on, over and/or around the base member.

The method may comprise forming a recess in the electrically conductive intermediate layer so as to define the waveguide path. The method may comprise forming the recess in the electrically conductive intermediate layer to a depth which is equal to, or substantially equal to, the thickness of the electrically conductive intermediate layer, or to a depth which is greater than the thickness of the electrically conductive intermediate layer.

The method may comprise locating an electrically insulating waveguide filler member in the recess.

Locating the electrically insulating waveguide filler member in the recess may comprise providing an electrically insulating waveguide filler material in the recess. For example, the locating the electrically insulating waveguide filler member in the recess may comprise providing a molten or liquid electrically insulating waveguide filler material in the recess, which molten or liquid electrically insulating waveguide filler material subsequently solidifies or sets so as to form the electrically insulating waveguide filler member.

The method may comprise forming an electrically conductive outer layer in situ on, over and/or around the electrically insulating waveguide filler member and the electrically conductive intermediate layer so that the electrically conductive intermediate layer and the electrically conductive outer layer together define the waveguide member.

The electrically conductive intermediate layer may comprise an electrically conductive material.

The electrically conductive intermediate layer may comprise an electrically insulating material and one or more electrically conductive reinforcing elements embedded within the electrically insulating material.

The one or more reinforcing elements of the electrically conductive intermediate layer may comprise one or more carbon fibres.

The electrically conductive outer layer may comprise conductive material.

The electrically conductive outer layer may comprise an electrically insulating material and one or more electrically conductive reinforcing elements embedded within the electrically insulating material.

The electrically insulating material of e electrically conductive outer layer may comprise the same electrically insulating material as the electrically conductive intermediate layer.

The electrically insulating material of the electrically conductive outer layer may be continuous with the electrically insulating material of the electrically conductive intermediate layer.

The one or more reinforcing elements of the electrically conductive outer layer may comprise one or more carbon fibres.

The method may comprise:
defining a recess in an outer surface of the base member; and
locating at least part of the electrically conductive waveguide member in the recess.

Locating at least part of the electrically conductive waveguide member in the recess may comprise providing an electrically conductive material in the recess. For example, locating at least part of the electrically conductive waveguide member in the recess may comprise providing a molten or liquid electrically conductive material in the recess, which molten or liquid electrically conductive material subsequently solidifies or sets so as to form at least part of the electrically conductive waveguide member. The electrically conductive material may comprise a metal.

The electrically conductive material may comprise at least one of copper, nickel, tin aluminium, zinc, iron, silver and gold.

The method may comprise forming an outer layer in situ on, over and/or around the base member and the waveguide member.

The outer layer may comprise an electrically insulating material and one or more reinforcing elements embedded within the matrix.

The electrically insulating material of the outer layer may comprise the same electrically insulating material as the base member.

The electrically insulating material of the outer layer and the electrically insulating material of the base member may be continuous.

The one or more reinforcing elements of the outer layer may be electrically conductive.

The one or more reinforcing elements of the outer layer may comprise one or carbon fibres.

The method may comprise forming one or more further recesses the electrically conductive intermediate layer, the further recesses being configured to accommodate at least one of a temperature sensor and a salinity sensor. The method may comprise forming the one or more further recesses in the electrically conductive intermediate layer to a sufficient depth so as to expose an outer surface of the base member and/or so as to extend partially into the base member.

The method may comprise locating at least one of a temperature sensor and a salinity sensor in the one or more further recesses.

The method may comprise forming the electrically conductive outer layer over and/or around at least one of the temperature sensor and the salinity sensor as to at least partially locate and/or embed at least one of the temperature sensor and the salinity sensor within the wall.

At least one of the inner region of the wall, the waveguide member, the waveguide filler member, the outer region of the wall and the outer member may comprise at least one of a polymer material, a thermoplastic material, a thermoset material, a polyaryl ether ketone, a polyaryl ketone, a polyether ketone (PEK), polyether ether ketone (PEEK), a polycarbonate, polyvinyl chloride (PVC), a polyamide, polyamide 11 (PA11), polyvinylidene fluoride, polyvinylidene difluoride (PVDF), polyphenylene suphide (PPS), polyethylenimines (PEI), polyoxymethylene (POM), acetal, a resin, a setting resin, a polymeric resin, and an epoxy resin.

BRIEF DESCRIPTION OF THE DRAWINGS

An apparatus and method for measuring a composition of a fluid will now be described by way of nonlimiting example only with reference to the accompanying drawings of which.

DETAILED DESCRIPTION OF THE DRAWINGS

Figure 1A:
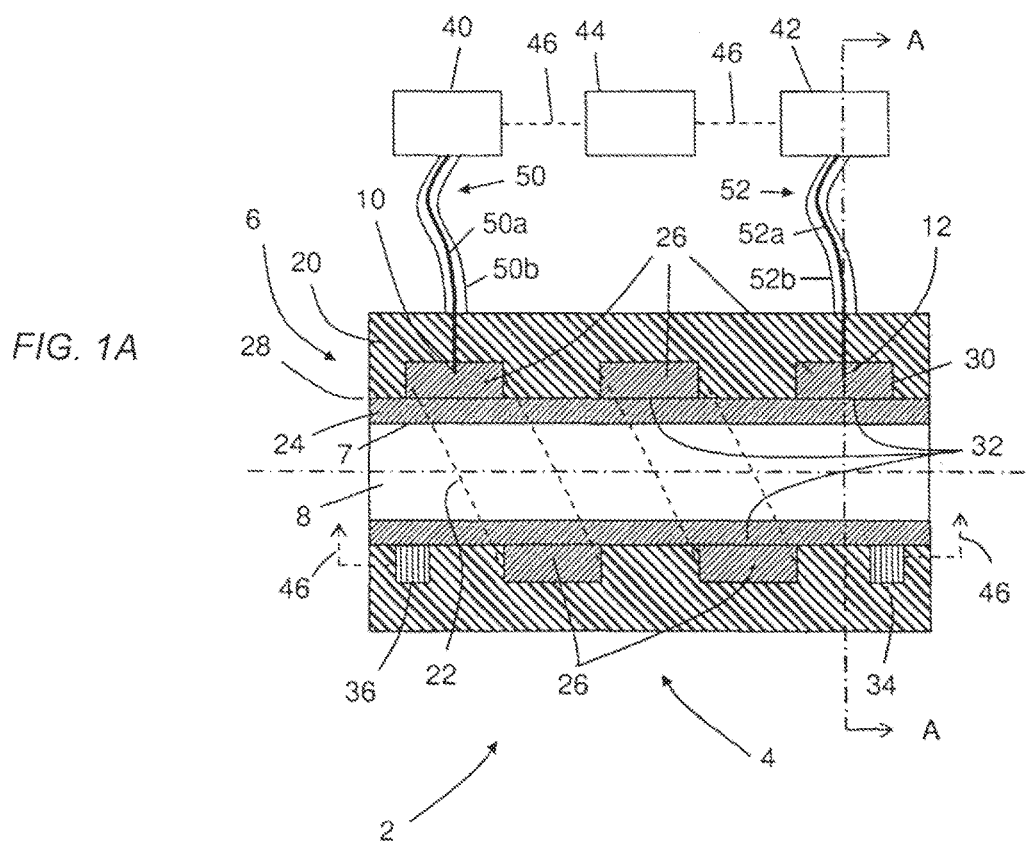
FIG. 1A is a schematic longitudinal cross-section of a first apparatus for measuring a composition of a fluid.
Figure 1B:
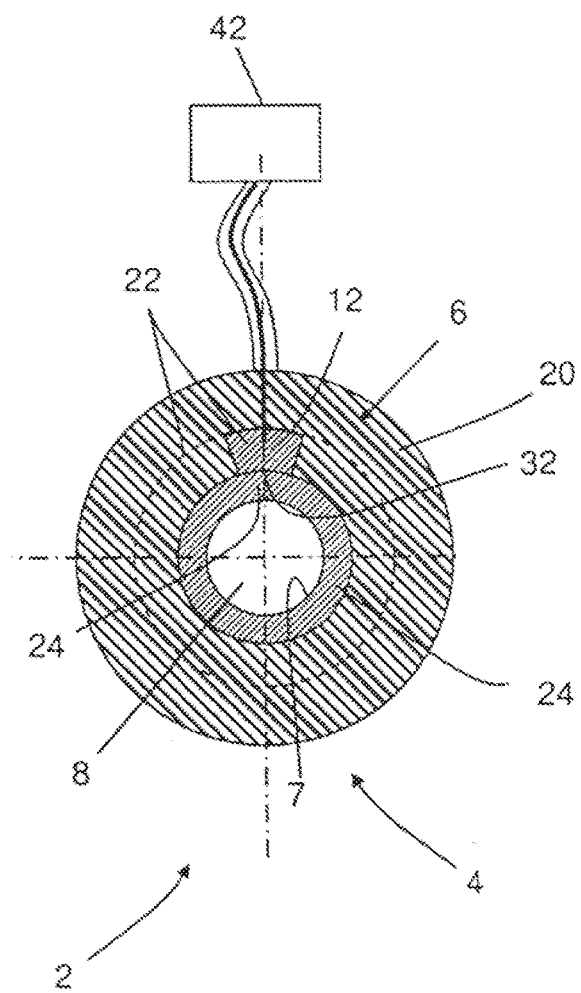
FIG. 1B is a schematic cross-section on AA of the first apparatus of FIG. 1A.

Referring initially to FIGS. 1A and 1B there is shown an apparatus generally designated 2 for measuring a composition of a fluid. The apparatus 2 includes a fluid conduit 4 having a wall 6. The wall has an inner surface 7 which defines a fluid flow path 8. The apparatus 2 includes a monopole transmitting antenna 10 and a monopole receiving antenna 12. The apparatus 2 further includes an electrically conductive waveguide member 20 which is electrically insulated from, but electromagnetically coupled to, the transmitting antenna 10 and the receiving antenna 12 for guiding an electromagnetic field from the transmitting antenna 10 to the receiving antenna 12 along a generally helical waveguide path 22 defined by the waveguide member 20. The waveguide member 20 is separated from the fluid flow path 8 by an electrically insulating inner region 24 of the wall 6. The inner region 24 of the wall 6 is formed from an electrically insulating PEEK material. A helical ridge 26 of the same electrically insulating PEEK material extends around an outer surface 28 of the inner region 24 of the wall 6. The waveguide member 20 extends over the helical ridge 26 and the outer surface 28 of the inner region 24 of the wall 6 so as to define a helical channel or groove 30 having an opening 32 which is disposed towards the fluid flow path 8. It should be understood that the waveguide member 20 is configured to not only guide the electromagnetic field along the waveguide path 22, but to also provide the fluid conduit 4 with sufficient strength to withstand internal fluid pressures existing within the fluid flow path 8 of up to 15,000 PSI. It should also be understood that the inner region 24 of the wall 6 effectively seals the waveguide member 20 from the fluid flow path 8, in addition, the inner surface 7 of the wall 6 is relatively smooth so as to suppress or reduce the build-up of deposits of solid matter such as hydrates, particulates or the like so as to prevent occlusion or restriction of the fluid flow path 8.

The apparatus 2 further includes a temperature sensor 34 located and/or embedded within the wall 6 of the fluid conduit 4 for sensing a temperature of a fluid present in and/or flowing through the fluid flow path 8 or for sensing a temperature of a region of the wall 6 of the fluid conduit 4 between the temperature sensor 34 and the fluid flow path 8. The apparatus 2 further includes a fluid salinity sensor 36 located and/or embedded within the wall 6 of the fluid conduit 4 for sensing a salinity of a fluid present in and/or flowing through the fluid flow path 8.

The apparatus 2 includes a radio frequency (RF) electrical signal generator 40 an electrical signal detector 42 and a controller 44. As illustrated by the dashed lines 46 in FIG. 1A, the controller 44 is configured for communication with the electrical signal generator 40, the electrical signal detector 42, the temperature sensor 34 and the salinity sensor 36. The apparatus 2 includes an input coaxial cable 50 which connects the electrical signal generator 40 to the fluid conduit 4. More specifically, the input coaxial cable 50 comprises an inner conductor 50a which electrically connects the electrical signal generator 40 to the transmitting antenna 10 and an outer tubular conductor 50b which electrically connects the electrical signal generator 40 to the waveguide member 20. The inner conductor 50a is electrically isolated from, and sealed with respect to, the waveguide member 20. Similarly, the apparatus 2 includes an output coaxial cable 52 which connects the electrical signal detector 42 to the fluid conduit 4. More specifically, the output coaxial cable 52 comprises an inner conductor 52a which electrically connects the receiving antenna 12 to the electrical signal detector 42 and an outer tubular conductor 52b which electrically connects the waveguide member 20 to the electrical signal detector 42. The inner conductor 52a is electrically isolated from, and sealed with respect to, the waveguide member 20.

In use, a fluid such as a two- or three-phase fluid is present in and/or flows through the fluid flow path 8. It should also be understood that, in use, the fluid conduit 4 is generally oriented vertically so that the composition of liquid close to the inner surface of the wall 6 is more closely representative of the composition of liquid in the fluid flow path 8 as a whole. The electrical signal generator 40 supplies an input electrical signal at a frequency of approximately 5 GHz to the transmitting antenna 10 via the input coaxial cable 40. The transmitting antenna 10 excites an electromagnetic field which is guided by the waveguide member 20 along the helical waveguide path 22 to the receiving antenna 12. A portion of the guided electromagnetic field extends laterally relative to the waveguide path 22 from the waveguide member 20, through the opening 32 and the inner region 24 of the wall 6 into the fluid flow path 6. An output electrical signal is induced in the receiving antenna 12 and is conveyed via the output coaxial cable 50 to the electrical signal detector 42. The electrical signal generator 40 communicates a magnitude or amplitude of the input electrical signal to the controller 44. The electrical signal detector 42 communicates a magnitude or amplitude of the output electrical signal to the controller 44. The controller 44 determines a measured energy loss of the electromagnetic field from the magnitude or amplitude of the input and output electrical signals. The controller 44 also receives a sensed value from the temperature sensor 34 and a sensed value from the salinity sensor 36. The sensed value received by the controller 44 from the temperature sensor 34 may, for example, be a measured temperature value. Alternatively, the controller 44 may use the sensed value received from the temperature sensor 34 together with temperature calibration data stored within the controller 44 to determine a measured temperature value. Similarly, the sensed value received by the controller 44 from the salinity sensor 36 may, for example, be a measured salinity value. Alternatively, the controller 44 may use the sensed value received from the salinity sensor 36 together with salinity calibration data stored within the controller 44 to determine a measured salinity value. At least one of the configuration of the waveguide member 20, the thickness of the inner region 24 of the wall 6, and the material of the inner region 24 of the wall 6 and frequency of the input electrical signal is selected so as to permit a portion of the electromagnetic field to extend laterally relative to the waveguide path 22 through the opening 32 and the inner region 24 of the wall 6 into the fluid flow path 8. The guided electromagnetic field loses energy as it is guided along the helical waveguide path 22 as a consequence of leakage of electromagnetic energy from the guided electromagnetic field through the opening and/or absorption of electromagnetic energy in the fluid in the fluid flow path 8. The energy loss during propagation of the electromagnetic field from the transmitting antenna 10 to the receiving antenna 12 is dependent upon the composition of the fluid. Specifically, it has been demonstrated that the loss increases with water-cut. It has also been demonstrated that the loss varies more weakly with fluid salinity and temperature.

Calibration data including electromagnetic energy loss as a function of water-cut, salinity and temperature is stored in the controller 44. The controller 44 uses the measured energy loss of the electromagnetic field and the measured temperature and salinity values together with the stored calibration data to determine the actual water-cut of the fluid in the fluid flow path 8.

Figure 2A:
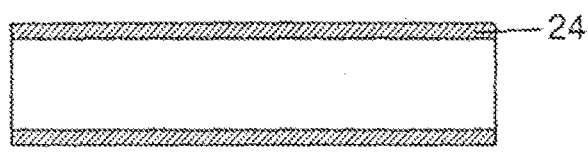
FIG. 2A illustrates a p in a method for manufacturing a fluid conduit of the first apparatus FIG. 1A.
Figure 2B:
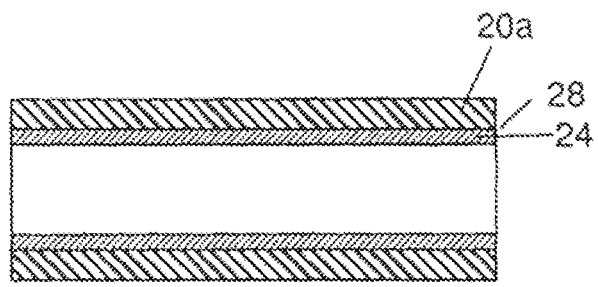
FIG. 2B illustrates a second step in the method for manufacturing the fluid conduit of the first apparatus of FIG. 1A.
Figure 2C:
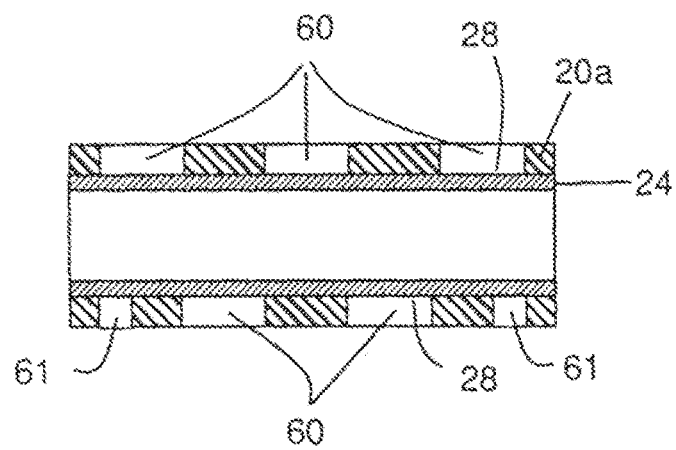
FIG. 2C illustrates a third step in the method for manufacturing the fluid conduit of the first apparatus of FIG. 1A.

FIGS. 2A-2F illustrate different steps in a method of manufacturing the fluid conduit 4 of the apparatus 2 of FIGS. 1A and B. As shown in FIG. 2A, the method of manufacture begins by providing a base member in the form of a PEEK sleeve 24. As shown in FIG. 2B, an electrically conductive inner composite layer 20a comprising carbon fibres embedded in a PEEK matrix is formed on the outer surface 28 of the PEEK sleeve 24 by applying a carbon fibre/PEEK tape around the outer surface 26 of the PEEK sleeve 24 so as to provide the carbon fibres with a predetermined angle relative to a longitudinal axis of the fluid conduit 4. The carbon fibre/PEEK tape is heated during application so as to melt or fuse the PEEK matrix of the tape with the PEEK matrix of any underlying layers of tape and/or the PEEK material of the sleeve 24. As shown in FIG. 2C, a helical recess 60 is formed in the inner composite layer 20a so as to expose a helical section of the outer surface 28 of the PEEK sleeve 24. The helical recess 60 is formed in a direction which is generally parallel to the direction of the carbon fibres. Without wishing to be bound by theory, it is thought that aligning the direction of the helical recess 60 with the direction of the carbon fibres may help to guide the electromagnetic field along the waveguide path 22 and reduce loss of electromagnetic energy through the waveguide member 20. One or more further recesses 61 are formed in the inner composite layer 20a for accommodating the temperature sensor 34 and the salinity sensor 36.

Figure 2D:
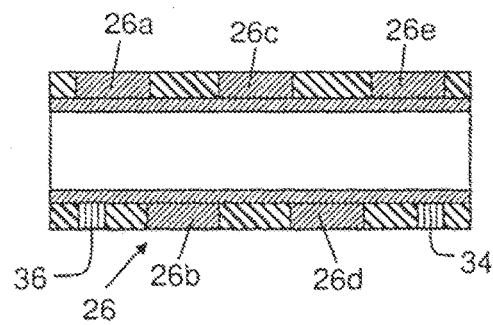
FIG. 2D illustrates a fourth step in the method for manufacturing the fluid conduit of the first apparatus of FIG. 1A.
Figure 2E:
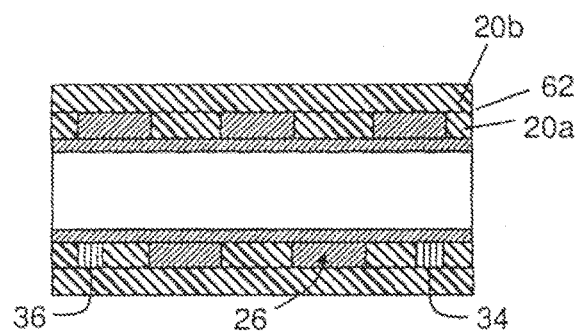
FIG. 2E illustrates a fifth step in the method for manufacturing the first apparatus of FIG. 1A.
Figure 2F:
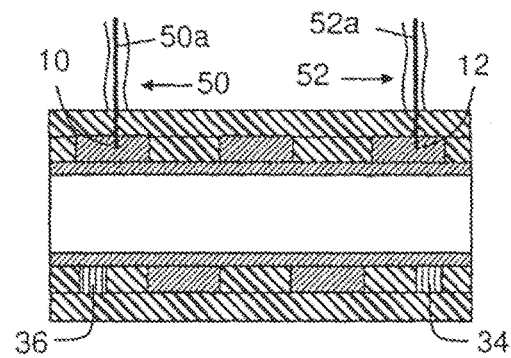
FIG. 2F illustrates a sixth step in the method for manufacturing the fluid conduit of the first apparatus of FIG. 1A.

As shown in FIG. 2D, PEEK inserts 26a, 26b, 26c, 26d, 26e are inserted into the helical recess 60. The PEEK inserts 26a, 26b, 26c, 26d, 26e are joined to one another, to the outer surface 28 of the PEEK sleeve 24 and/or to the sides of the helical recess 60 defined in the inner composite layer 20a by bonding or fusing so as to form the helical ridge 20. The temperature sensor 34 and the salinity sensor 36 are inserted into the further recesses 61. As shown in FIG. 2E, an electrically conductive outer composite layer 20b comprising carbon fibres embedded in a PEEK matrix is formed over an outer surface 62 of the inner composite layer 20a, the PEEK inserts 26a, 26b, 26c, 26d, 26e, the temperature sensor 34 and the salinity sensor 36 by wrapping a carbon fibre/PEEK tape around the outer surface 62 and heating the applied tape so as to melt or fuse the PEEK matrix of the tape with the PEEK matrix of any underlying layers of tape, the PEEK material of the inner composite layer 20a and the PEEK material of the PEEK inserts 26a, 26b, 26c, 26d, 26e, As shown FIG. 2F, manufacture of the fluid conduit 4 is completed with the formation of the transmitting antenna 10 and the formation of the receiving antenna 12. It should be understood that an end of the inner conductor 50a of the input coaxial cable 50 is located within the helical ridge 26 so as to define the transmitting antenna 10 and an end of the inner conductor 52a of the output coaxial cable 52 is located within the helical ridge 26 so as to define the receiving antenna 12. It should be understood that respective holes are defined in the outer composite layer 20b and the helical ridge 26 and that the inner conductors 50a, 52a of the input and output coaxial cables 50, 52 extend through, and are electrically isolated from and sealed relative to, the respective holes so as to define the antennas 10, 12.

It should also be understood that as a consequence of the manufacturing process of the fluid conduit 4 described above with reference to FIGS. 2A-2F, the PEEK material of the PEEK sleeve 24, the PEEK material of the inner composite layer 20a and the PEEK material of the outer composite layer 20b may be fused together so as to form a continuous PEEK matrix throughout a thickness of the wall 6 of the fluid conduit 4. As such, the inner and outer composite layers 20a, 20b are unitary (and may be indistinguishable) so as to define the waveguide member 20. Similarly, the PEEK sleeve 24 may also be considered to be unitary with the waveguide member 20 so that the PEEK sleeve 24 may be considered to form the inner region 24 of the wall 6 of the fluid conduit 4. Also, depending on the exact nature of the bonding or fusing process used to join the PEEK inserts 26a, 26b, 26c, 26d, 26e to one another, to the outer surface 28 of the PEEK sleeve 24 and/or to the sides of the helical recess 60 defined in the inner composite layer 20a, the PEEK material of each PEEK insert 26a, 26b, 26c, 26d, 26e may be fused with the PEEK material of at least one other PEEK insert 26a, 26b, 26c, 26d, 26e, the PEEK material of the sleeve 24, the PEEK material of the inner composite layer 20a and the PEEK material of the outer composite layer 20b.

Figure 3A:
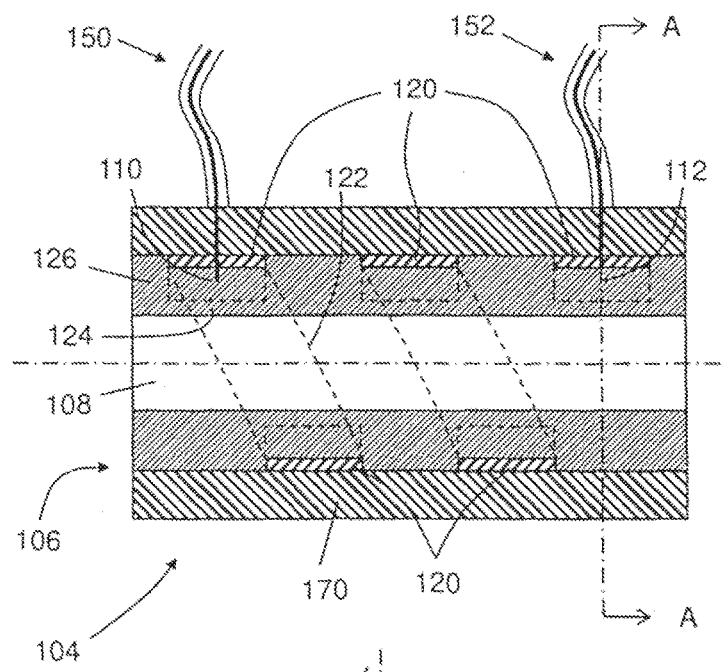
FIG. 3A is a schematic longitudinal cross-section of a fluid conduit of a second apparatus for measuring a composition of a fluid.
Figure 3B:
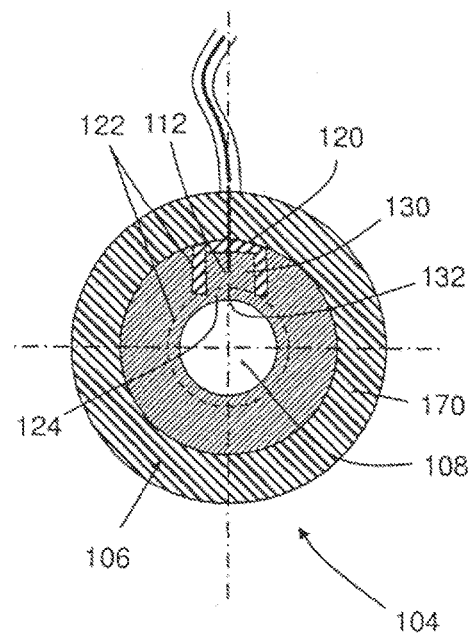
FIG. 3B is a schematic cross-section on of the fluid conduit of FIG. 3A.

FIGS. 3A and 3B show a fluid conduit 104 of a first alternative apparatus for measuring the composition of a fluid. The fluid conduit 104 of FIGS. 3A and 3B shares many corresponding features with the fluid conduit 4 of FIGS. 1A and 1B with like features of the fluid conduit 104 having the same reference numerals as the corresponding features of the fluid conduit 4 incremented by "100". The fluid conduit 104 has a wall 106 which defines a fluid flow path 108. A monopole transmitting antenna 110 and a monopole receiving antenna 112 are embedded within the wall 106. The fluid conduit 104 further includes an electrically conductive waveguide member 120 which is electrically insulated from, but electromagnetically coupled to, the transmitting antenna 110 and the receiving antenna 112 for guiding an electromagnetic field from the transmitting antenna 110 to the receiving antenna 112 along a general helical waveguide path 122 defined by the waveguide member 120. The waveguide member 120 is embedded within a PEEK layer 126 of the wall 126 and is separated from the fluid flow path 105 by an electrically insulating inner region 124 of the PEEK layer 126 of the wall 106. The waveguide member 120 has a generally uniform U-shaped lateral cross-section in a plane lateral to the waveguide path 122. The waveguide member 120 defines a helical channel or groove 130 having an opening 132 which is disposed towards the fluid flow path 108. An outer structural layer 170 of carbon fibres embedded in a PEEK matrix is formed around the waveguide member 120 and the PEEK layer 126. It should be understood that the outer structural layer 170 provides the fluid conduit 104 with sufficient strength to withstand internal fluid pressures existing within the fluid flow path 108 of up to 15,000 PSI.

It should be understood that at least one of a temperature sensor (not shown) and a fluid salinity sensor (not shown) may be at least partially located and/or embedded within the wall 106 of the fluid conduit 104. The fluid conduit 104 may be electrically connected to an electrical signal generator (not shown) and an electrical signal detector (not shown) via input and output coaxial cables 150 152 respectively for measurement of loss of the electromagnetic field guided by the waveguide member 120 and for determination of the water-cut of a fluid present in and/or flowing through the fluid flow path 108 in a similar manner to that already described above with reference to the fluid conduit 4 of FIGS. 1A and 1B.

Figure 4A:
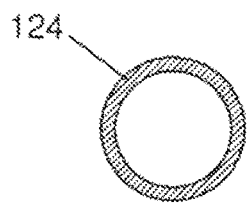
FIG. 4A illustrates a first step in the method for manufacturing the fluid conduit of FIG. 3A.
Figure 4B:
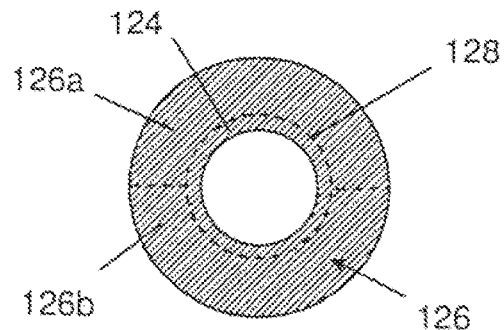
FIG. 4B illustrates a second step in the method manufacturing the fluid conduit of FIG. 3A.
Figure 4C:
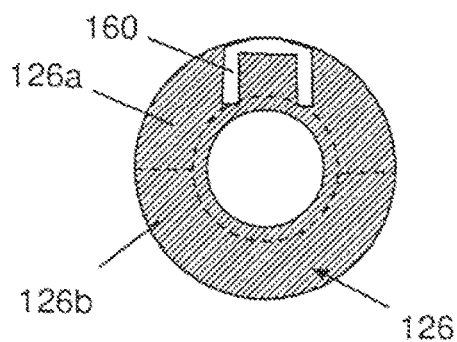
FIG. 4C illustrates a third step in the method for manufacturing the fluid conduit of FIG. 3A.
Figure 4D:
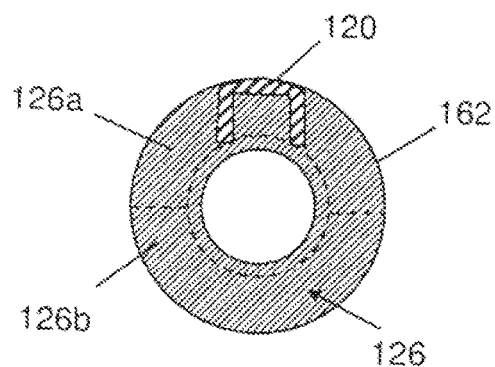
FIG. 4D illustrates a fourth step in the method for manufacturing the fluid conduit of FIG. 3A.
Figure 4E:
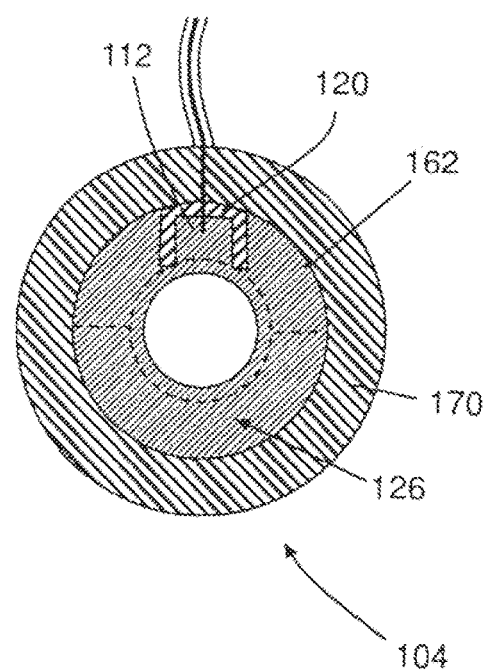
FIG. 4E illustrates a fifth step in the method for manufacturing the fluid conduit of FIG. 3A.

FIGS. 4A-4E illustrate different steps in a method of manufacturing the fluid conduit 104 of FIGS. 3A and 3B. As shown in FIG. 4A, the method of manufacture begins by providing a base member in the form of a PEEK sleeve 124. As shown in FIG. 4B, an electrically insulating PEEK layer 126 is formed on the outer surface 128 of the PEEK sleeve 124 by assembling and bonding two PEEK half-pipe members 126a, 126b to the outer surface 128 of the PEEK sleeve 124. As shown in FIG. 4O, a generally helical recess 160 is formed in the PEEK layer 126 with a generally uniform U-shaped lateral cross-section. As shown in FIG. 4D, an electrically conductive material such as copper is injected or inserted into the helical recess 160 so as to define the waveguide member 120. As shown in FIG. 4E, the carbon fibre/PEEK outer structural layer 170 is formed over an outer surface 162 of the waveguide member 120 and the PEEK layer 126 by wrapping a carbon fibre/PEEK tape around the outer surface 162 and heating the applied tape so as to melt or fuse the PEEK matrix of the tape with the PEEK matrix of any underlying layers of tape and/or the PEEK material of the PEEK layer 126. Manufacture of the fluid conduit 104 is completed with the formation of the transmitting antenna 110 and the formation of the receiving antenna 112.

Figure 5A:
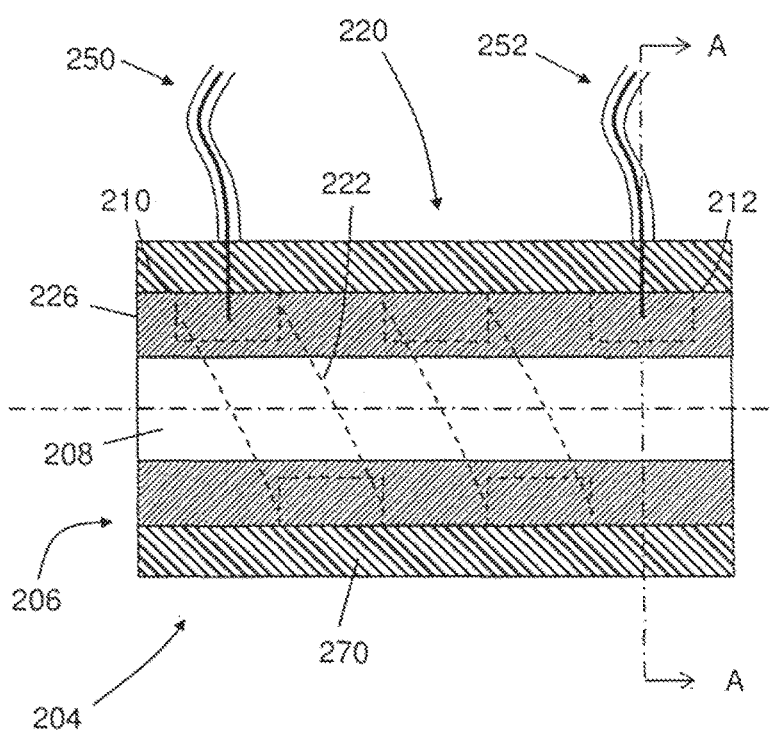
FIG. 5A is a schematic longitudinal cross-section of a fluid conduit of a third apparatus for measuring a composition of a fluid.
Figure 5B:
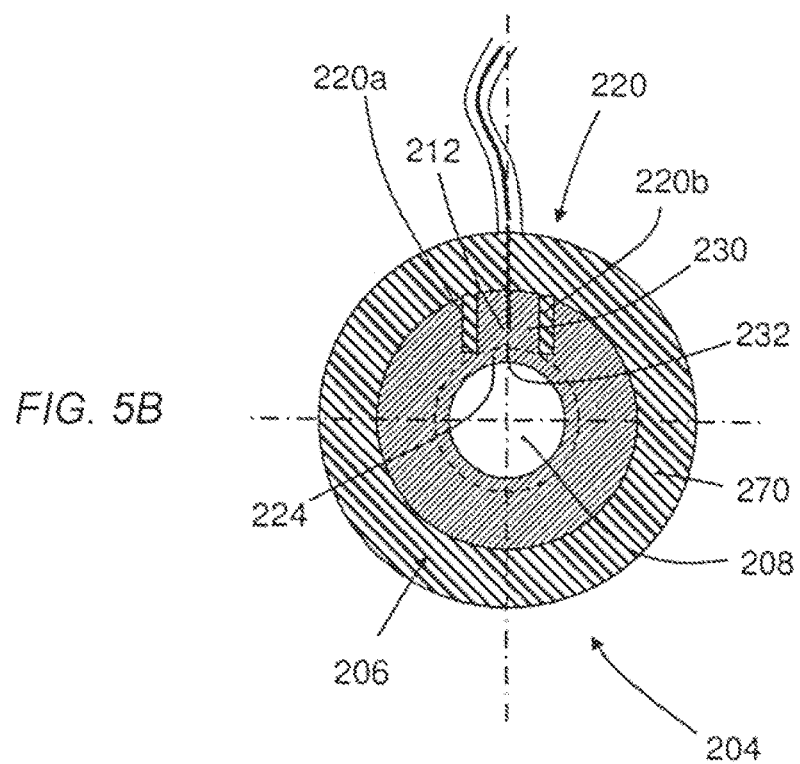
FIG. 5B is a schematic cross-section on AA of the fluid conduit of FIG. 5A.

FIGS. 5A and 5B show a fluid conduit 204 of a second alternative apparatus for measuring the composition of a fluid. The fluid conduit 204 of FIGS. 5A and 5B shares many corresponding features with the fluid conduit 104 of FIGS. 3A and 3B with like features of the fluid conduit 204 having the same reference numerals as the corresponding features of the fluid conduit 104 incremented by "100". The fluid conduit 204 has a wall 206 which defines a fluid flow path 208. A monopole transmitting antenna 210 and a monopole receiving antenna 212 are embedded within the wall 206. The fluid conduit 204 further includes electrically conductive waveguide members 220a, 220b embedded within a PEEK layer 226 of the wall 206. The waveguide members 220a, 220b are separated from the fluid flow path 208 by an electrically insulating inner region 224 of the PEEK layer 226 of the wall 206. An electrically conductive outer structural layer 270 of carbon fibres embedded in a PEEK matrix is formed around the waveguide members 220a, 220b and the PEEK layer 226. It should be understood that the electrically conductive outer structural layer 270 not only provides the fluid conduit 204 with sufficient strength to withstand internal fluid pressures existing within the fluid flow path 208 of up to 15,000 PSI but, together with the waveguide members to 220a, 220b, also defines an electrically conductive waveguide member generally designated 220. The waveguide member 220 is electrically insulated from, but electromagnetically coupled to, the transmitting antenna 210 and the receiving antenna 212 for guiding an electromagnetic field from the transmitting antenna 210 to the receiving antenna 212 along a generally helical waveguide path 222 defined by the waveguide member 220. The waveguide member 220 defines a helical channel or groove 230 having an opening 232 which is disposed towards the fluid flow path 208.

It should be understood that at least one of a temperature sensor (not shown) and a fluid salinity sensor (not shown) may be at least partially located and/or erg bedded within the wall 206 of the fluid conduit 204. The fluid conduit 204 may be electrically connected to an electrical signal generator (not shown) and an electrical signal detector (not shown) via input and output coaxial cables 250, 262 respectively for measurement of loss of the electromagnetic field guided by the waveguide member 220 and for determination of the water-cut of a fluid present in and/or flowing through the fluid flow path 208 in a similar manner to that already described above with reference to the fluid conduit 4 of FIGS. 1A and 1B.

Figure 6A:
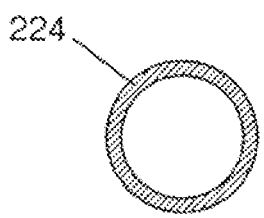
FIG. 6A illustrates a first step in a method for manufacturing the fluid conduit of FIG. 5A.
Figure 6B:
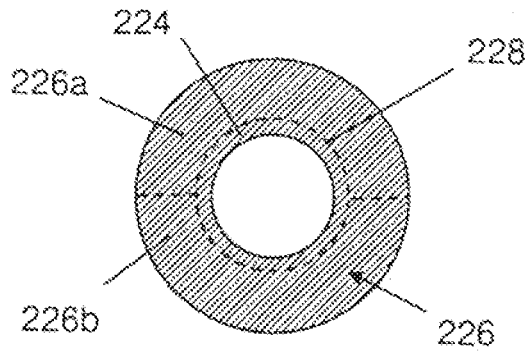
FIG. 6B illustrates a second step in the method for manufacturing the fluid conduit of FIG. 5A.
Figure 6C:
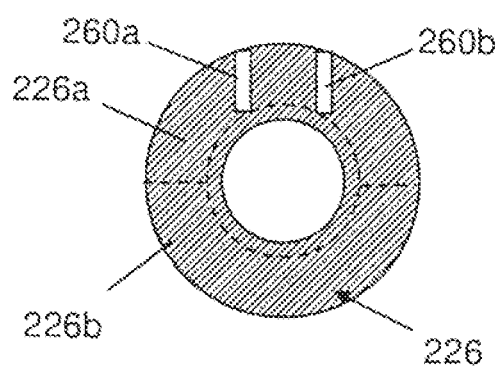
FIG. 6C illustrates a third step in the method for manufacturing the fluid conduit of FIG. 5A.
Figure 6D:
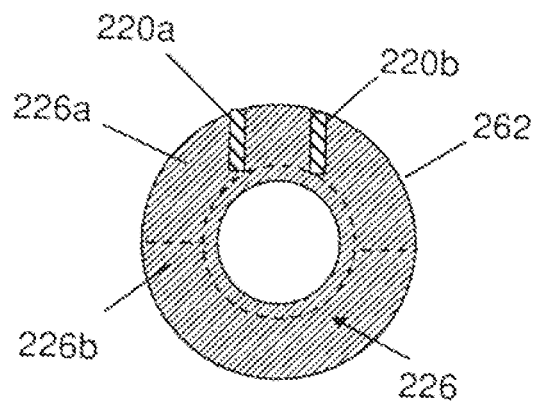
FIG. 6D illustrates a fourth step in the method for manufacturing the fluid conduit of FIG. 5A.
Figure 6E:
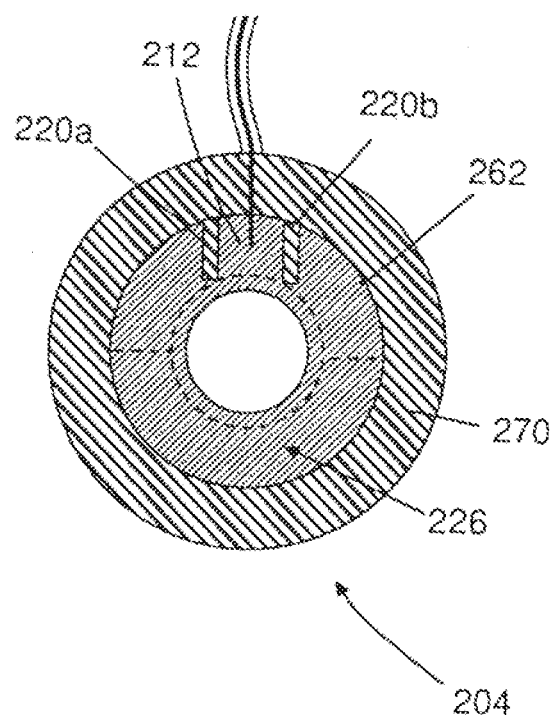
FIG. 6E illustrates a fifth step in the method for manufacturing the fluid conduit of FIG. 5A.

FIGS. 6A-6E illustrate different steps in a method of manufacturing the fluid conduit 204 of FIGS. 5A and 5E. As shown in FIG. 6A, the method of manufacture begins by providing a base member in the form of a PEEK sleeve 224. As shown in FIG. 6B, an electrically insulating PEEK layer 226 is formed on the outer surface 228 of the PEEK sleeve 224 by assembling and bonding two PEEK half-pipe members 226a, 226b to the outer surface 228 of the PEEK sleeve 224. As shown in FIG. 6C, two parallel generally helical recesses 260a, 260b are formed in the PEEK layer 226. As shown in FIG. 6D, an electrically conductive material such as copper is injected or inserted into the helical recesses 260a, 260b. As shown in FIG. 6E, the electrically conductive carbon fibre/PEEK outer structural layer 270 is formed over an outer surface 262 of the waveguide members 220a, 220b and the PEEK layer 226 by wrapping a carbon fibre/PEEK tape around the outer surface 262 and heating the applied tape so as to melt or fuse the PEEK matrix of the tape with the PEEK matrix of any underlying layers of tape and/or the PEEK material of the PEEK layer 226. Manufacture of the fluid conduit 204 is completed with the formation of the transmitting antenna 210 and the formation of the receiving antenna 212.

One of ordinary skill in the art will understand that various modifications of the foregoing apparatus and methods are possible. For example, the input electrical signal may have any frequency in the range 1 to 10 GHz, 2.5 to 7.5 GHz, or 4 to 6 GHz. The waveguide path 22 may have a geometry other than helical. For example, the waveguide path 22 may extend along and/or around the sleeve 24. The waveguide path 22 may be generally straight. The waveguide path 22 may extend parallel to a longitudinal axis of the fluid conduit. The waveguide path 22 may extend along a circular arc. The waveguide path 22 may extend circumferentially relative to the longitudinal axis of the fluid conduit. The waveguide path 22 may be generally circular. The waveguide path 22 may encircle or circumscribe the sleeve 24 one or more times. The waveguide path 22 may encircle or circumscribe the longitudinal axis of the fluid conduit one or more times.

The inner or sleeve 24 of the 6 of the fluid conduit 4 may include an electrically insulating material or a dielectric material of any kind. For example, the inner region or sleeve 24 of the wall 6 of the fluid conduit 4 may comprise at least one of a polymer material, a thermoplastic material, a thermoset material, a polyaryl ether ketone, a polyaryl ketone, a polyether ketone (PEK), a polyether ether ketone (PEEK), a polycarbonate, polyvinyl chloride (PVC), a polyamide, polyamide 11 (PA11), polyvinylidene fluoride, polyvinylidene difluoride (PVDF), polyphenylene suphide PPS), polyethylenimines (PEI), polyoxymethylene (POW, acetal, a resin, a setting resin, a polymeric resin, and an epoxy resin. The electrically insulating material may include a matrix and one or more reinforcing elements embedded within the matrix. The one or more reinforcing elements may be electrically insulating. For example, the one or more reinforcing elements may include at least one of polymeric fibres, aramid fibres, non-polymeric fibres, basalt fibres, glass fibres and E-glass fibres.

The waveguide 20 may include a matrix material comprising any of the electrically insulating materials of which the sleeve 24 may comprise. The waveguide member 20 may comprise one or more metal reinforcing elements.

The apparatus may comprise a temperature sensor which is located separately from the fluid conduit 4. For example, the apparatus may comprise a temperature sensor connected to a pipe which is coupled to one end of the fluid conduit 4. Similarly, the apparatus may comprise a fluid salinity sensor which is located separately from the fluid conduit 4. For example, the apparatus may comprise a fluid salinity sensor connected to a pipe which is coupled to one end of the fluid conduit 4.

The apparatus may comprise a plurality of transmitting antennae, a plurality of receiving antennae, and a plurality of electrically conductive waveguide members. Each waveguide member may be separated from the fluid flow path by the electrically insulating inner region of the wall. Each waveguide member may be electrically insulated from, but electromagnetically coupled to, a corresponding one of the transmitting antennae and a corresponding one of the receiving antennae, for guiding a corresponding electromagnetic field from the corresponding transmitting antenna to the corresponding receiving antenna along a corresponding waveguide path. Each waveguide member may define a corresponding opening which is disposed towards the fluid flow path to permit a portion of the corresponding electromagnetic field to extend through the corresponding opening and the inner region of the wall into the fluid flow path.

The invention claimed is:

1. An apparatus for measuring a composition of a fluid, comprising:
    a fluid conduit having a wall which defines a fluid flow path;
    a transmitting antenna;
    a receiving antenna; and
    an electrically conductive waveguide member configured for electromagnetic coupling with the transmitting antenna and the receiving antenna and for guiding an electromagnetic field from the transmitting antenna to the receiving antenna along a waveguide path,
    wherein the waveguide member is separated from the fluid flow path by an electrically insulating inner region of the wall and the waveguide member defines an opening which is disposed towards the fluid flow path to permit a portion of the electromagnetic field to extend through the opening and the inner region of the wall into the fluid flow path,
    wherein the waveguide member defines a helical groove disposed towards the fluid flow path and the helical groove defines the opening.

2. The apparatus according to claim 1, wherein the opening extends along the whole of the waveguide path.

3. The apparatus according to claim 1, wherein the waveguide member has a generally uniform cross-section.

4. The apparatus according to claim 1, wherein the waveguide member has a generally U-shaped cross-section.

5. The apparatus according to claim 1, wherein at least one of the configuration of the waveguide member, a thickness of the inner region of the wall, a material of the inner region of the wall and a frequency of the electromagnetic field is selected so as to permit the electromagnetic field to extend through the opening and the inner region of the wall into the fluid flow path.

6. The apparatus according to claim 1, wherein the waveguide path:
    extends along and/or around the fluid flow path;
    extends along a straight line or comprises a section which extends along a straight line;
    extends along a circular arc or comprises a section which extends along a circular arc;
    is circular or comprises a section which is circular;
    encircles or circumscribes the fluid flow path one or more times or comprises a section which encircles or circumscribes the fluid flow path one or more times; and/or
    is helical or generally helical or comprises a section which is helical or generally helical.

7. The apparatus according to claim 1, wherein the waveguide path:
    extends parallel to a longitudinal axis of the fluid conduit or comprises a section which extends parallel to the longitudinal axis of the fluid conduit;
    extends circumferentially relative to the longitudinal axis of the fluid conduit or comprises a section which extends circumferentially relative to the longitudinal axis of the fluid conduit;
    encircles or circumscribes the longitudinal axis of the fluid conduit one or more times or comprises a section which encircles or circumscribes the longitudinal axis of the fluid conduit one or more times; and/or
    extends helically or generally helically relative to the longitudinal axis of the fluid conduit or comprises a section which extends helically or generally helically relative to the longitudinal axis of the fluid conduit.

8. The apparatus according to claim 1, wherein the inner region of the wall seals the waveguide member from the fluid flow path.

9. The apparatus according to claim 1, wherein the transmitting antenna is at least partially located and/or embedded within the wall and/or wherein the receiving antenna is at least partially located and/or embedded within the wall.

10. The apparatus according to claim 1, wherein the electrically conductive waveguide member is at least partially located and/or embedded within the wall and/or wherein the electrically conductive waveguide member defines part of the wall.

11. The apparatus according to claim 1, wherein the inner region of the wall comprises an electrically insulating material.

12. The apparatus according to claim 10, wherein the inner region of the wall comprises the electrically insulating material and one or more electrically insulating reinforcing elements embedded within the electrically insulating material.

13. The apparatus according to claim 11, wherein the one or more electrically insulating reinforcing elements comprise at least one of polymeric fibres, aramid fibres, non-polymeric fibres, basalt fibres, glass fibres and E-glass fibres.

14. The apparatus according to claim 13, wherein the waveguide member comprises an electrically insulating material and one or more electrically conductive reinforcing elements embedded within the electrically insulating matrix material.

15. The apparatus according to claim 14, wherein the electrically insulating material of the inner region of the wall and the electrically insulating material of the waveguide member comprise the same electrically insulating material and/or wherein the electrically insulating material of the waveguide member is continuous with the electrically insulating material of the inner region of the wall.

16. The apparatus according to claim 14, wherein the one or more electrically conductive reinforcing elements comprise one or more carbon fibres.

17. The apparatus according to claim 14, wherein the one or more electrically conductive reinforcing elements have a common orientation relative to the waveguide path and/or wherein the one or more electrically conductive reinforcing elements are arranged generally parallel to the waveguide path.

18. The apparatus according to claim 17, wherein the waveguide member comprises a metal.

19. The apparatus according to claim 18, wherein the wall comprises an outer region.

20. The apparatus according to claim 19, wherein the outer region of the wall is located externally of the waveguide member or wherein the outer region of the wall defines at least part of the waveguide member.

21. The apparatus according to claim 19, wherein the outer region of the wall comprises a composite material comprising an electrically insulating material and one or more reinforcing elements embedded within the electrically insulating material.

22. The apparatus according to claim 21, wherein the electrically insulating material of the outer region of the wall and the electrically insulating material of the waveguide member comprise the same electrically insulating material.

23. The apparatus according to claim 22, wherein the electrically insulating material of the outer region of the wall is continuous with the electrically insulating material of the waveguide member.

24. The apparatus according to claim 23, wherein the fluid conduit comprises a base member which defines the electrically insulating inner region of the wall.

25. The apparatus according to claim 24, wherein the base member is generally tubular or comprises a sleeve.

26. The apparatus according to claim 24, wherein the waveguide member is located externally of the base member, the transmitting antenna is located externally of the base member and/or the receiving antenna is located externally of the base member.

27. The apparatus according to claim 24, wherein the waveguide path extends along and/or around the base member, wherein the waveguide path encircles or circumscribes the base member one or more times and/or wherein the waveguide path extends helically or generally helically around the base member.

28. The apparatus according to claim 24, wherein the opening is disposed towards the base member.

29. The apparatus according to claim 28, wherein the fluid conduit comprises an electrically insulating waveguide filler member, wherein the waveguide filler member extends from an outer surface of the base member to an inner surface of the waveguide member.

30. The apparatus according to claim 29, wherein the waveguide member defines a channel or a groove disposed towards the fluid flow path and the channel or the groove defines the opening;
wherein the waveguide filler member extends from the outer surface of the base member into the channel or the groove and/or wherein the waveguide filler member fills the channel or the groove.

31. The apparatus according to claim 29, wherein the waveguide filler member is formed in situ on, over and/or around the base member.

32. The apparatus according to claim 29, wherein the waveguide filler member is formed separately from the base member and is then fitted on, over and/or around the base member.

33. The apparatus according to claim 29, wherein the waveguide filler member is bonded, adhered, fused, welded and/or joined to the base member.

34. The apparatus according to claim 29, wherein the waveguide filler member comprises the same electrically insulating material as the base member and/or the waveguide member, and/or wherein the electrically insulating material of the waveguide filler member is continuous with the electrically insulating material of the base member and/or the electrically insulating material of the waveguide member.

35. The apparatus according to claim 29, wherein the transmitting antenna extends into and/or is at least partially embedded within the waveguide filler member and/or wherein the receiving antenna extends into and/or is at least partially embedded within the waveguide filler member.

36. The apparatus according to claim 29, wherein the waveguide member is formed in situ on, over and/or around the waveguide filler member.

37. The apparatus according to claim 29, wherein the waveguide member is formed separately from the waveguide filler member and is then fitted on, over and/or around the waveguide filler member.

38. The apparatus according to claim 29, wherein the waveguide member is bonded, adhered, fused, welded and/or joined to the waveguide filler member.

39. The apparatus according to claim 19, wherein the fluid conduit comprises an outer member which defines the outer region of the wall.

40. The apparatus according to claim 39, wherein the outer member is formed in situ on, over and/or around the waveguide member.

41. The apparatus according to claim 39, wherein the outer member is formed separately from the waveguide member and is then fitted on, over and/or around the waveguide member.

42. The apparatus according to claim 39, wherein the outer member is bonded, adhered, fused, welded and/or joined to the waveguide member.

43. The apparatus according to claim 39, wherein the outer member comprises an electrically insulating material and one or more reinforcing elements embedded within the electrically insulating material.

44. The apparatus according to claim 43, wherein the electrically insulating material of the outer member comprises the same electrically insulating material as the waveguide member and/or wherein the electrically insulating material of the outer member is continuous with the electrically insulating material of the waveguide member.

45. The apparatus according to claim 44, wherein the one or more reinforcing elements of the outer member are electrically conductive and/or wherein the one or more reinforcing elements of the outer member comprise one or more carbon fibres.

46. The apparatus according to claim 1, wherein the fluid conduit is configured to withstand one or more environmental conditions associated with a fluid in an oil or gas well and/or wherein the fluid conduit is configured to withstand a pressure within the fluid flow path of up to 15,000 PSI, up to 10,000 PSI, or up to 5,000 PSI.

47. The apparatus according to claim 1, wherein the fluid conduit is configured to withstand a temperature within the fluid flow path of up to 200° C., of up to 150° C. or of up to 100° C.

48. The apparatus according to claim 1, comprising
a plurality of transmitting antennae;
a plurality of a receiving antennae; and
a plurality of electrically conductive waveguide members, each waveguide member being configured for electromagnetic coupling with a corresponding one of the transmitting antennae and a corresponding one of the receiving antennae and for guiding a corresponding electromagnetic field from the corresponding transmitting antenna to the corresponding receiving antenna along a corresponding waveguide path, and
wherein each waveguide member is separated from the fluid flow path by the electrically insulating inner region of the wall and each waveguide member defines a corresponding opening which is disposed towards the fluid flow path to permit a portion of the corresponding electromagnetic field to extend through the corresponding opening and the inner region of the wall into the fluid flow path.

49. The apparatus according to claim 48, wherein at least one of the inner region of the wall, the waveguide member, the waveguide filler member, the outer region of the wall and the outer member comprises at least one of a polymer material, a thermoplastic material, a thermoset material, a polyaryl ether ketone, a polyaryl ketone, a polyether ketone (PEK), a polyether ether ketone (PEEK), a polycarbonate, polyvinyl chloride (PVC), a polyamide, polyamide 11 (PA11), polyvinylidene fluoride, polyvinylidene difluoride (PVDF), polyphenylene sulphide (PPS), polyethylenimines (PEI), polyoxymethylene (POM), acetal, a resin, a setting resin, a polymeric resin, and an epoxy resin.

50. The apparatus according to claim 1, wherein the electromagnetic field has a radio frequency (RF) and/or wherein the electromagnetic field has a frequency in the range 1 to 10 GHz, 2.5 to 7.5 GHz, 4 to 6 GHz or has a frequency of approximately 5 GHz.

51. A method for measuring a composition of a fluid, comprising: providing a fluid in a fluid flow path defined by a wall of a fluid conduit;
electromagnetically coupling a transmitting antenna and a receiving antenna with an electrically conductive waveguide member;
guiding an electromagnetic field from the transmitting antenna to the receiving antenna along a waveguide path defined by the waveguide member,
wherein the waveguide member is separated from the fluid flow path by an electrically insulating inner region of the wall and the waveguide member defines an opening which is disposed towards the fluid flow path to permit a portion of the electromagnetic field to extend through the opening and the inner region of the wall into the fluid flow path,
wherein the waveguide member defines a helical groove disposed towards the fluid flow path and the helical groove defines the opening.

52. The method according to claim 51, comprising:
providing an input electrical signal to the transmitting antenna;
measuring an output electrical signal received at the receiving antenna; and
determining an electromagnetic loss from the input electrical signal and the measured output electrical signal.

53. The method according to claim 52, comprising:
determining the composition of the fluid from the determined electromagnetic loss and a known relationship between the composition of the fluid and the electromagnetic loss.

54. The method according to claim 52, comprising determining relative proportions of different liquid components of the fluid from the determined electromagnetic loss and a known relationship between the relative proportions of the different liquid components and the electromagnetic loss.

55. The method according to any one of claim 52, comprising determining a proportion of water by volume in the liquid phase of the fluid from the determined electromagnetic loss and a known relationship between the proportion of water by volume in the liquid phase of the fluid and the electromagnetic loss.

56. The method according to claim 52, comprising:
measuring a temperature of the fluid and/or a temperature of the wall adjacent to the fluid flow path.

57. The method according to claim 52, comprising:
measuring a salinity of the fluid.

58. The method according to claim 56, comprising:
measuring a salinity of the fluid; and
determining the composition of the fluid from the determined electromagnetic loss, at least one of the measured temperature and the measured salinity, and a known relationship between the composition of the fluid, the electromagnetic loss and at least one of the temperature and the salinity.

59. The method according to claim 51, wherein the input and output electrical signals are radio frequency (RF) electrical signals and/or wherein the input and output electrical signals have a frequency in the range 1 to 10 GHz, 2.5 to 7.5 GHz, 4 to 6 GHz or a frequency of approximately 5 GHz.

60. The method according to claim 51, wherein the fluid is a two-phase or a three-phase fluid and/or wherein the fluid comprises water and at least one of oil and gas.

61. The method according to claim 60, wherein the fluid comprises a mixture of liquids of which the proportion of water is in the range 50% to 100%.

62. The method according to claim 51, comprising orienting the fluid conduit vertically or near vertically and/or mixing the fluid present in and/or flowing through the fluid flow path.

63. A method for manufacturing an apparatus for measuring a composition of a fluid, the method comprising:
providing a fluid conduit having a wall which defines a fluid flow path;
providing a transmitting antenna;
providing a receiving antenna; and
providing an electrically conductive waveguide member which is configured for electromagnetic coupling with the transmitting antenna and the receiving antenna and for guiding an electromagnetic field from the transmitting antenna to the receiving antenna along a waveguide path,
wherein the waveguide member is separated from the fluid flow path by an electrically insulating inner region of the wall and the waveguide member defines an opening which is disposed towards the fluid flow path to permit a portion of the electromagnetic field to extend through the opening and the inner region of the wall into the fluid flow path,
wherein the waveguide member defines a helical groove disposed towards the fluid flow path and the helical groove defines the opening.

64. The method according to claim 63, comprising at least partially locating and/or embedding the transmitting antenna within the wall and/or at least partially locating and/or embedding the receiving antenna within the wall.

65. The method according to claim 63, wherein the electrically conductive waveguide member defines part of the wall and/or wherein the electrically conductive waveguide member is at least partially located and/or embedded within the wall.

66. The method according to claim 63, comprising providing an electrically insulating base member which defines the fluid flow path.

67. The method according to claim 66, comprising:
forming an electrically conductive intermediate layer in situ on, over and/or around the base member;
forming a recess in the electrically conductive intermediate layer so as to define the waveguide path;
locating an electrically insulating waveguide filler member in the recess; and
forming an electrically conductive outer layer in situ on, over and/or around the electrically insulating waveguide filler member and the electrically conductive intermediate layer so that the electrically conductive intermediate layer and the electrically conductive outer layer together define the waveguide member.

68. The method according to claim 67, comprising forming the recess in the electrically conductive intermediate layer to a depth which is equal to, or substantially equal to, the thickness of the electrically conductive intermediate layer, or to a depth which is greater than the thickness of the electrically conductive intermediate layer.

69. The method according to claim 66, comprising:
defining a recess in an outer surface of the base member;
locating at least part of the electrically conductive waveguide member in the recess.

70. The method according to claim 69, comprising:
forming an outer layer in situ on, over and/or around the base member and the waveguide member.

71. The method according to claim 67, wherein the outer layer comprises an electrically insulating material and one or more reinforcing elements embedded within the electrically insulating material.

72. The method according to claim 71, wherein the one or more reinforcing elements of the outer layer are electrically conductive.

73. The method according to claim 72, wherein the one or more reinforcing elements of the outer layer comprise one or more carbon fibres.

* * * * *